Dec. 6, 1966 R. L. BYRUM Plant Pat. 2,689
ROSE PLANT
Filed Oct. 25, 1965
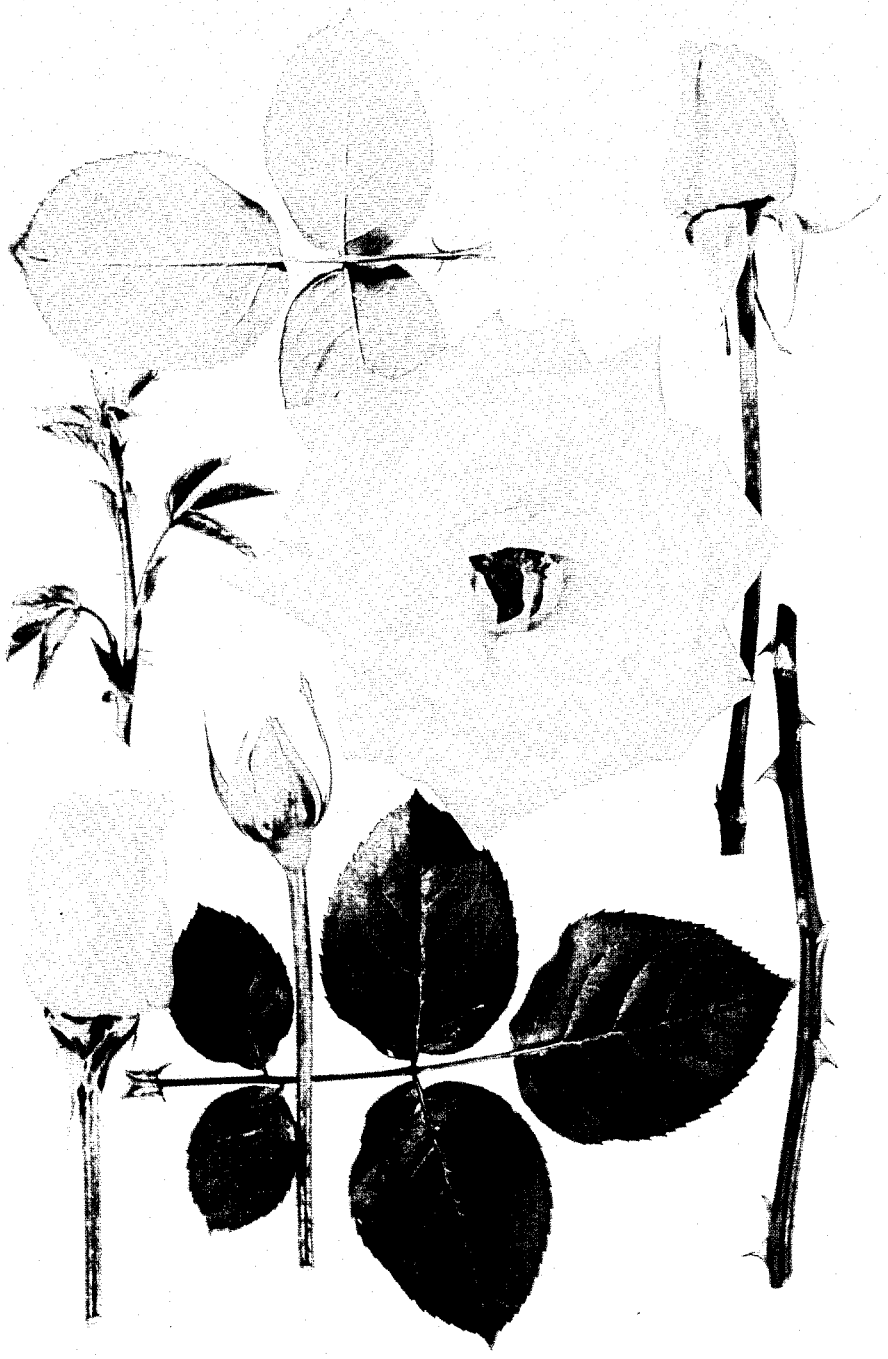
Inventor.
Roy L. Byrum
By: Robb & Robb
Attorneys.

United States Patent Office

Plant Pat. 2,689
Patented Dec. 6, 1966

2,689
ROSE PLANT

Roy L. Byrum, Richmond, Ind., assignor to Joseph H. Hill Company, Richmond, Ind., a corporation of Indiana Filed Oct. 25, 1965, Ser. No. 505,197
1 Claim. (Cl. Plt.—17)

The present invention relates to a new and distinct variety of rose plant of the hybrid tea class, which was originated by me by crossing an unnamed and unpatented seedling of unidentified parentage, but designated in my breeding records as #57–14R, with the variety known as "Jaqueline" (Plant Patent No. 2,183), the unnamed seedling being the seed parent and the variety "Jaqueline" being the pollen parent.

The primary objective of this breeding was to produce a new and improved rose variety which bears flowers of the size and color of the seed parent, but combined with the good growth and habits of the pollen parent. This objective was fully achieved, along with other desirable improvements, as evidenced by the following unique combination of characteristics which are outstanding in the new variety and which distinguish it from its parents, as well as from all other varieties of which I am aware:

(1) A very vigorous habit of growth;
(2) Abundant foliage;
(3) Long flower stems;
(4) Large flowers of attractive Vermilion color;
(5) Excellent flower keeping qualities; and
(6) Exceptional suitability for year-around greenhouse forcing use, with consequent ability to hold the flower size and color in hot summer months, yet with good flower production in the dark winter days.

In comparison with its unnamed seed parent, the new variety maintains more uniform production, with the flowers borne on longer stems throughout the year, than in the case of this parent, while maintaining the bright red color and large size of the flowers comparable to this parent.

As compared with its pollen parent, "Jaqueline," the new variety has inherited the vigorous growth and good flower production of this parent, but produces larger flowers of a different and unusual Vermilion color, said color being in the same color range as the flowers of the variety known as "Tropicana," Plant Patent No. 1,969, but varying considerably from the latter variety in plant growth.

Asexual reproduction of my new variety by grafting, as performed at Richmond, Indiana, and also by budding, as performed at West Grove, Pennsylvania shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as (W)), and Koster's Color Guide (hereinafter abbreviated as (K)), except where general color terms of ordinary dictionary significance are obvious:

Type: Greenhouse; bush; seedling.
Class: Hybrid tea.
Breeding: Seedling.
*Seed parent.*—An unnamed seedling identified as #57–14R.
*Pollen parent.*—"Jaqueline."

Propagation: Holds its distinguishing characteristics through succeeding propagations by both grafting and budding.

*Flower*

Locality where grown and observed: Richmond, Indiana.
Flowers borne: Singly to stem; on long, strong stems.
Quantity of bloom: Abundant, in greenhouse.
Continuity: Continuous, in greenhouse.
Fragrance: Slight. Nature—tea.
Bud:
*Peduncle.*—Medium length; medium caliper; strong; erect. Bark—smooth; color—Scheele's Green, Plate 860 (W). Thorns—none. Prickles—numerous; color—nearest Uranium Green, Plate 63/3 (W). Hairs—none.
*Before calyx breaks.*—Size—medium large. Form—ovoid; with a conspicuous neck; with foliaceous appendages on the surface of the bud; with stout foliaceous parts extending beyond the tip of the bud equal to ¼ of its length. Color—Geranium Lake, Plate 20 (W).
*As calyx breaks.*—Color (outside of petal)—Delft Rose, Plate 020/1 (W), with shades of Currant Red, Plate 821/1 (W).
*As first petal opens.*—Size—large. Form—ovoid. Color: Outside—Scarlet, Plate 19/1 (W); inside—Mandarin Red, Plate 17 (W).
*Opening.*—Opens well in greenhouse.
Bloom:
*Size (when fully open).*—Large; from 4 inches to 5 inches.
*Petalage.*—Double; from 25 to 35 petals; arranged regularly.
*Form.*—Full and high-centered at first, but becoming flat and open; petals being at first tightly rolled outward, but later becoming loosely rolled outward at maturity.
Petals:
*Texture.*—Moderately thick.
*Appearance.*—Inside—satiny. Outside—shiny.
*Shape.*—Outer petals—obovate, with apex retuse and with 1 notch. Intermediate petals—obovate, with apex obtuse. Inner petals—obovate, with apex retuse and with 1 notch.

This description of a newly opened flower was made from a rose grown in a greenhouse during the month of July at Richmond, Indiana:

*Color.*—Outer petals: Outside surface—Porcelain Rose, Plate 620 (W); inside surface—Vermilion, Plate 18/1 (W). Intermediate petals: Outside surface—Porcelain Rose, Plate 620 (W); inside surface—Vermilion, Plate 18/1 (W). Inner petals: Outside surface—Porcelain Rose Plate 620 (W), with center vein of Tyrian Rose, Plate 24/2 (W); inside surface—Vermilion, Plate 18/1 (W).

This description was made from a rose that was open for three days in a greenhouse during the month of August at Richmond, Indiana:

*Color.*—Outer petals: Outside surface—base almost white, gradually changing through Empire Rose, Plate 0621/1 (W) to Empire Rose, Plate 0621 (W); inside surface—Azalea Pink, Plate 618 (W). Intermediate petals: Outside surface—base almost white, changing to Empire Rose, Plate 0621/1 (W); inside surface—Begonia, Plate 619 (W). Inner petals: Outside surface—Porcelain Rose, Plate 620 (W), with vein of Phlox Pink, Plate 625/2 (W); inside surface—Begonia, Plate 619 (W).
*Behavior.*—Persist, in greenhouse.

*Flower longevity.*—Cut roses grown in greenhouse and kept at living room temperatures—4 or 5 days in July.

*General color effect.*—Newly opened flower— Vermilion, Plate 18/1 (W). There days open—Begonia, Plate 619/1 (W).

*Plant*

Foliage:

*Leaves.*—Abundant; compound of 5–7 leaflets; large size; heavy.

*Leaflets.*—Shape—ovoid. Apex—mucronate. Base—round. Margin—simply serrate.

*Color.*—Mature: Upper surface—nearest Spinach Green, Plate 0960 (W); under surface—nearest Cedar Green, Plate 80 (K). Young: Upper surface—Lettuce Green, Plate 861/3 (W), with outside of leaf overlaid with Oxblood Red, Plate 00823/3 (W); under surface—nearest Oxblood Red, Plate 00823/3 (W), with blotches of Pod Green, Plate 061/2 (W) along center vein.

*Rachis (the supporting stem of the compound leaf).*—Medium heavy. Upper side—grooved. Under side—moderately prickly.

*Stipules.*—Short; narrow; with moderately short points turning out at an angle of about 45°.

Growth (in greenhouse):

*Habit.*—Bush; upright; much-branched.

*Growth.*—Vigorous.

*Canes.*—Large diameter.

*Main stems.*—Color—most Spinach Green, Plate 0960 (W), but some Spinach Green, Plate 0960 (W) with streaks of Van Dyck Brown, Plate 96 (K). Thorns—several; medium length; hooked downward; with long, narrow base; color—Bistre, Plate 93 (K). Prickles—none. Hairs—none.

*Branches.*—Color—Spinach Green, Plate 0960/1 (W). Thorns—several; medium length; hooked downward; with long, narrow base; color—base Violet Lilac, Plate 47 (K), gradually changing to Sap Green, Plate 62/3 (W) at tip. Prickles—few; color—Violet Lilac, Plate 47 (K). Hairs—none.

*New shoots.*—Color—Scheele's Green, Plate 860/3 (W). Thorns—several; medium length; hooked downward; with long, narrow base; color—Poppy Red, Plate 16/3 (W). Prickles—few; color—Poppy Red, Plate 16/3 (W). Hairs—none.

*Reproductive organs*

Stamens: Medium number; arranged regularly about pistils.

Filaments: Medium length; most with anthers. Color—Crimson Carmine, Plate 41 (K).

Anthers: All open at once; large size. Color—Yellow Ochre, Plate 07/2 (W).

Pollen: Abundant. Color—Yellow Ochre, Plate 07/1 (W).

Pistils: Medium number.

Styles: Uneven; medium length; medium heavy; bunched. Color—Tyrian Rose, Plate 24/1 (W).

Stigma: Color—Pure White, Plate 1 (K).

Ovularies: All enclosed in calyx.

Hips: None.

Sepals: Permanent; long; straight; spear-shaped. Color: Inside—Scheele's Green, Plate 860 (W), overlaid and edged with white fuzz and with a lighter vein of Scheele's Green, Plate 860/3 (W) through center; outside—Scheele's Green, Plate 860 (W).

Seeds: None.

I claim:

A new and distinct variety of rose plant of the hybrid tea class, substantially as herein shown and described, characterized particularly as to novelty by the unique combination of a very vigorous habit of growth, abundant foliage, long flower stems, large flowers of attractive Vermilion color, excellent flower keeping qualities, and exceptional suitability for year-around greenhouse forcing use, with consequent ability to hold the flower size and color in hot summer months, yet with good flower production in the dark winter days.

No references cited.

ABRAHAM S. STONE, *Primary Examiner.*

R. E. BAGWILL, *Assistant Examiner.*